(12) United States Patent
Ten Kate et al.

(10) Patent No.: US 9,011,352 B2
(45) Date of Patent: Apr. 21, 2015

(54) FALL DETECTION AND/OR PREVENTION SYSTEMS

(75) Inventors: Warner Rudolph Theophile Ten Kate, Eindhoven (NL); Heribert Baldus, Aachen (DE); Sheng Jin, Shanghai (CN); Yang Peng, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 694 days.

(21) Appl. No.: 13/059,484

(22) PCT Filed: Aug. 20, 2009

(86) PCT No.: PCT/IB2009/053677
§ 371 (c)(1),
(2), (4) Date: Jun. 13, 2011

(87) PCT Pub. No.: WO2010/023604
PCT Pub. Date: Mar. 4, 2010

(65) Prior Publication Data
US 2011/0230791 A1    Sep. 22, 2011

(30) Foreign Application Priority Data
Aug. 28, 2008    (EP) .................................... 08163139

(51) Int. Cl.
*A61B 5/11*    (2006.01)
*G08B 21/04*    (2006.01)
*G08B 29/22*    (2006.01)

(52) U.S. Cl.
CPC .......... *G08B 21/0446* (2013.01); *A61B 5/1117* (2013.01); *G08B 29/22* (2013.01)

(58) Field of Classification Search
CPC ........................... A61B 5/1117; A61B 5/1116
USPC ......................................... 600/300, 301, 595
See application file for complete search history.

(56) References Cited

U.S. PATENT DOCUMENTS

| | | | |
|---|---|---|---|
| 6,208,251 B1 * | 3/2001 | Cadet et al. ................. | 340/573.1 |
| 6,561,992 B1 * | 5/2003 | Eberhart et al. .............. | 600/595 |
| 7,289,857 B2 * | 10/2007 | Nauck et al. .................... | 700/30 |
| 7,612,681 B2 * | 11/2009 | Azzaro et al. .............. | 340/573.4 |

(Continued)

FOREIGN PATENT DOCUMENTS

| | | |
|---|---|---|
| EP | 1071055 | 1/2001 |
| EP | 1779772 | 5/2007 |

(Continued)

OTHER PUBLICATIONS

"Fall detection—Principles and Methods" Noury et al. Proceedings of the 29th Annual International Conference of the IEEE EMBS Cite Internationale, Lyon, France Aug. 23-26, 2007.*

*Primary Examiner* — Sean Dougherty
*Assistant Examiner* — Michael C Stout

(57) ABSTRACT

There is provided a fall detection and/or prevention system, comprising one or more sensors for detecting characteristics of movement of a user of the fall detection and/or prevention system and for generating corresponding signals; processing means for analyzing the signals from the one or more sensors using a fall detection algorithm to determine if a fall has taken place or is likely to take place; wherein the processing means is further adapted to update said fall detection algorithm based on the result of the analysis of the signals and an indication whether a fall has actually taken place from the user or a third party.

18 Claims, 5 Drawing Sheets

(56) References Cited

U.S. PATENT DOCUMENTS

| | | | |
|---|---|---|---|
| 7,627,451 B2* | 12/2009 | Vock et al. | 702/178 |
| 7,981,058 B2* | 7/2011 | Akay | 600/595 |
| 8,152,745 B2* | 4/2012 | Smith et al. | 600/595 |
| 2002/0091326 A1* | 7/2002 | Hashimoto et al. | 600/483 |
| 2002/0101349 A1 | 8/2002 | Rojas, Jr. | |
| 2002/0175499 A1* | 11/2002 | Mattes | 280/728.1 |
| 2003/0045782 A1* | 3/2003 | Iliff | 600/300 |
| 2004/0230105 A1* | 11/2004 | Geva et al. | 600/301 |
| 2004/0249249 A1* | 12/2004 | Lawson et al. | 600/300 |
| 2005/0110648 A1 | 5/2005 | Lehrman et al. | |
| 2005/0195079 A1* | 9/2005 | Cohen | 340/539.12 |
| 2006/0001545 A1* | 1/2006 | Wolf | 340/573.1 |
| 2006/0049950 A1 | 3/2006 | Lockhart | |
| 2006/0195201 A1* | 8/2006 | Nauck et al. | 700/30 |
| 2006/0252999 A1* | 11/2006 | Devaul et al. | 600/300 |
| 2006/0270949 A1* | 11/2006 | Mathie et al. | 600/595 |
| 2006/0282021 A1* | 12/2006 | DeVaul et al. | 600/595 |
| 2007/0093989 A1* | 4/2007 | Nashner | 702/185 |
| 2007/0132597 A1 | 6/2007 | Rodgers | |
| 2008/0108913 A1 | 5/2008 | Lengsfeld et al. | |
| 2008/0129518 A1* | 6/2008 | Carlton-Foss | 340/573.1 |
| 2008/0161651 A1* | 7/2008 | Peterson et al. | 600/300 |
| 2008/0272918 A1* | 11/2008 | Ingersoll | 340/573.1 |
| 2008/0294019 A1* | 11/2008 | Tran | 600/301 |
| 2009/0031803 A1* | 2/2009 | Noda et al. | 73/488 |
| 2009/0143704 A1* | 6/2009 | Bonneau et al. | 600/595 |
| 2009/0216156 A1* | 8/2009 | Lengsfeld et al. | 600/595 |
| 2009/0221937 A1* | 9/2009 | Smith et al. | 600/595 |
| 2009/0306741 A1* | 12/2009 | Hogle et al. | 607/54 |
| 2009/0326339 A1* | 12/2009 | Horvitz | 600/301 |
| 2010/0100004 A1* | 4/2010 | van Someren | 600/549 |
| 2010/0268125 A9* | 10/2010 | Epley | 600/595 |
| 2010/0286572 A1* | 11/2010 | Moersdorf et al. | 600/595 |

FOREIGN PATENT DOCUMENTS

| | | |
|---|---|---|
| GB | 2323196 | 3/1997 |
| GB | 2352815 | 2/2001 |
| JP | 9028681 A | 2/1997 |
| JP | 2002175581 | 6/2002 |
| JP | 2005173668 A | 6/2005 |
| JP | 04668684 B2 | 4/2011 |
| WO | WO2005027488 | 3/2005 |
| WO | WO2007081629 | 7/2007 |

* cited by examiner

FALL DETECTION AND/OR PREVENTION SYSTEMS

TECHNICAL FIELD OF THE INVENTION

The invention relates to fall detection and/or prevention systems, and in particular to a fall detection and/or prevention system having a fall detection algorithm that can be adapted to the characteristics of a particular user.

BACKGROUND TO THE INVENTION

Falling is a significant problem in the care of the elderly that can lead to morbidity and mortality. From a physical perspective, falls causes injuries, while from the mental perspective, falls causes fear-of-falling, which in turn leads to social isolation and depression.

In terms of intervention, there are two aspects where electronic devices can assist. One is to provide an automated and reliable fall detection system, and the other is to provide a fall prevention system that provides early feedback to the user or the user's care provider if the user engages in a (more) risky situation. The first assures adequate measures will be taken in case of a fall incident, which also provides a level of reassurance to the user, and the second assists the user in staying healthy, which provides a further level of reassurance. Fall detection systems are becoming widely available, and fall prevention systems are expected to appear shortly.

Commonly, automated fall detection systems are centered around an accelerometer which is to be attached to the user's body. The detector tracks the signals from the accelerometer and determines that a fall has taken place if a characteristic pattern is identified. A typical pattern is a combination of a high impact value in which the acceleration signal exceeds a preconfigured threshold, followed by a period of relatively constant acceleration, for example gravity only, since the user is lying motionless on the ground. The pattern may continue by revealing activity, deviating from the relatively constant period, when the user stands up again.

Several refinements and extensions exist to this simple system. For example, gyroscopes and/or magnetometers can be used to measure the body's orientation to check for a sustained non-vertical position in evaluating whether a fall has occurred.

Current automatic fall detection systems are typically equipped with an "alarm-reset" button that the user can press to suppress false alarms (false positives—FP) before they reach a care provider, so that further intervention by the care provider is aborted. Often, the alarm-reset button, or alternatively an "alarm" button, is used to enable the user to request assistance, which, in a way, indicates a missed alarm (i.e. a false negative—FN). These two functions can appear as two separate buttons for the user to press. They can also be integrated in one physical button, in which case the function switches with the current state of the detection algorithm (no-fall versus fall detected). It should be noted however that the buttons are not required to be part of the device attached to the user's body. They could also be part of a base station, located in the home of the user, to which the sensor communicates and which further transmits an alarm to the care provider's call centre. It makes most sense to mount the button for the reset function on the base station and to have the alarm function with the sensor.

One problem with automatic fall detection systems is the reliable classification of falls and non-falls, characterized through sensitivity and specificity. Clearly, for reliable classification, false positives and false negatives should be suppressed as much as possible. Full reliability (i.e. no FP or FN) is only achievable if the characteristics of the signal feature set can be distinguished completely in two separate sets, one characterizing a fall incident, the other a non-fall incident. Obviously, in fall prevention, the system cannot make use of the high acceleration events in the signal, since they will not (yet) be present, and the problem of correct identification of increased risk situations is even more difficult.

Many techniques to arrive at correct classifications are known. They are collectively referred to as machine learning [T. M. Mitchell, *Machine Learning*, McGraw-Hill, 1997]. In these methods, an algorithm is designed that classifies value combinations of features from the sensor signals as characterizing a fall or a non-fall. Using feature sets that are known to correspond to a fall or non-fall, the algorithm's parameters are adapted to provide a correct response to this training data. The amount of adaptation is usually derived from a statistical analysis of the algorithm, so that the update process converges to a situation that matches an optimality criterion. Of course, in order to be perfectly successful, it is required that the signals, i.e. their observed features, are distinguishable in the ideal, i.e. noise-free, situation. If this is not the case, errors (FP and FN) will fundamentally remain, and the task is to find an optimal setting trading these FP and FN. For an effective training of the algorithm, a sufficient amount of data samples are needed, so that the classification boundaries can be optimized for the variance in the feature set.

A problem that remains concerns the acquisition of the reference data so that it is of sufficient size and sufficiently represents the classes to be distinguished. Since people move in different ways, and hence will generate different signals and patterns, it is hard to provide a "one-size-fits-all" set of reference data.

Therefore, it is an object of the invention to provide a fall detection and/or prevention system that can be adapted to a particular user's fall or activity characteristics in order to improve the reliability of the fall detection algorithm, without requiring the user to spend a dedicated period of time training the detector. It is a further object of the invention to provide a fall detection and/or prevention system that can adapt to changes in the user's activity characteristics (for example, due to ageing).

SUMMARY OF THE INVENTION

In accordance with a first aspect of the invention, there is provided a fall detection and/or prevention system, comprising one or more sensors for detecting characteristics of movement of a user of the fall detection and/or prevention system and for generating corresponding signals; processing means for analyzing the signals from the one or more sensors using a fall detection algorithm to determine if a fall has taken place or is likely to take place; wherein the processing means is further adapted to update said fall detection algorithm based on the result of the analysis of the signals and an indication whether a fall has actually taken place from the user or a third party.

Therefore, as an indication of whether a fall has actually taken place is compared with the result of the fall detection algorithm, the fall detection algorithm can be updated in order to reduce the incidence of false positives and false negatives.

Preferably, the processing means is adapted to generate an alarm signal in the event that a fall has taken place or is likely to take place.

In a preferred embodiment, the system further comprises a memory for storing the signals, an indication from the fall detection algorithm of whether the fall detection algorithm has determined that a fall has taken place or is likely to take place and the indication whether a fall has actually taken place.

In a further embodiment, the system further comprises means for generating a trace for a plurality of signals from the one or more sensors, and the memory is adapted to store the trace of the signals.

Preferably, the indication whether a fall has actually taken place comprises a reset signal.

Preferably, the processing means determines that the fall detection algorithm has provided a false positive in the event that the fall detection algorithm detects that a fall has taken place and the reset signal is present, and the processing means is adapted to update the fall detection algorithm accordingly.

Preferably, the processing means determines that the fall detection algorithm has provided a true positive in the event that the fall detection algorithm detects that a fall has taken place and the reset signal is not present, and the processing means is adapted to update the fall detection algorithm accordingly.

In a further embodiment, the system further comprises means for receiving the reset signal from a third party.

In a further embodiment, the system further comprises a first user operable component for allowing a user to selectively generate the reset signal.

In a further preferred embodiment, the system further comprises a second user-operable component for generating an alarm signal.

Preferably, the processing means determines that the fall detection algorithm has provided a false negative in the event that the fall detection algorithm does not detect that a fall has taken place and the alarm signal is present, and the processing means is adapted to update the fall detection algorithm accordingly.

Preferably, the processing means determines that the fall detection algorithm has provided a true positive in the event that the fall detection algorithm detects that a fall has taken place and the alarm signal is present, and the processing means is adapted to update the fall detection algorithm accordingly.

Preferably, the fall detection algorithm comprises one or more feature sets representing signals from the one or more sensors.

Preferably, the processing means is adapted to monitor the frequency with which the fall detection algorithm is updated, and if the frequency exceeds a threshold, the processing means is adapted to remove one or more feature sets from the fall detection algorithm.

Preferably, the processing means determines if a fall has taken place or is likely to take place by comparing the one or more feature sets with the corresponding signals generated by the one or more sensors.

Preferably, the processing means is adapted to update the fall detection algorithm in order to selectively optimize false positives, where the algorithm incorrectly detects a fall, false negatives, where the algorithm incorrectly detects that no fall has taken place, or to obtain a stable ratio between false positives and false negatives.

A second aspect of the invention provides a method of training a fall detection and/or prevention algorithm for use in a fall detection and/or prevention system, the method comprising obtaining measurements of characteristics of movement of a user of the fall detection and/or prevention system; analyzing the measurements using a fall detection algorithm to determine if a fall has taken place or is likely to take place; and updating the fall detection algorithm based on the result of the step of analyzing and an indication whether a fall has actually taken place from the user or a third party.

A third aspect of the invention provides a computer program product comprising executable code that, when executed on a suitable computer or processor, performs the steps of receiving signals indicating characteristics of movement of a user of a fall detection and/or prevention system; analyzing the signals using a fall detection algorithm to determine if a fall has taken place or is likely to take place; and updating said fall detection algorithm based on the result of the analysis of the signals and an indication whether a fall has actually taken place received from the user or a third party.

BRIEF DESCRIPTION OF THE DRAWINGS

The invention will now be described, by way of example only, with reference to the following drawings, in which.

DETAILED DESCRIPTION OF THE PREFERRED EMBODIMENTS

Figure 1:
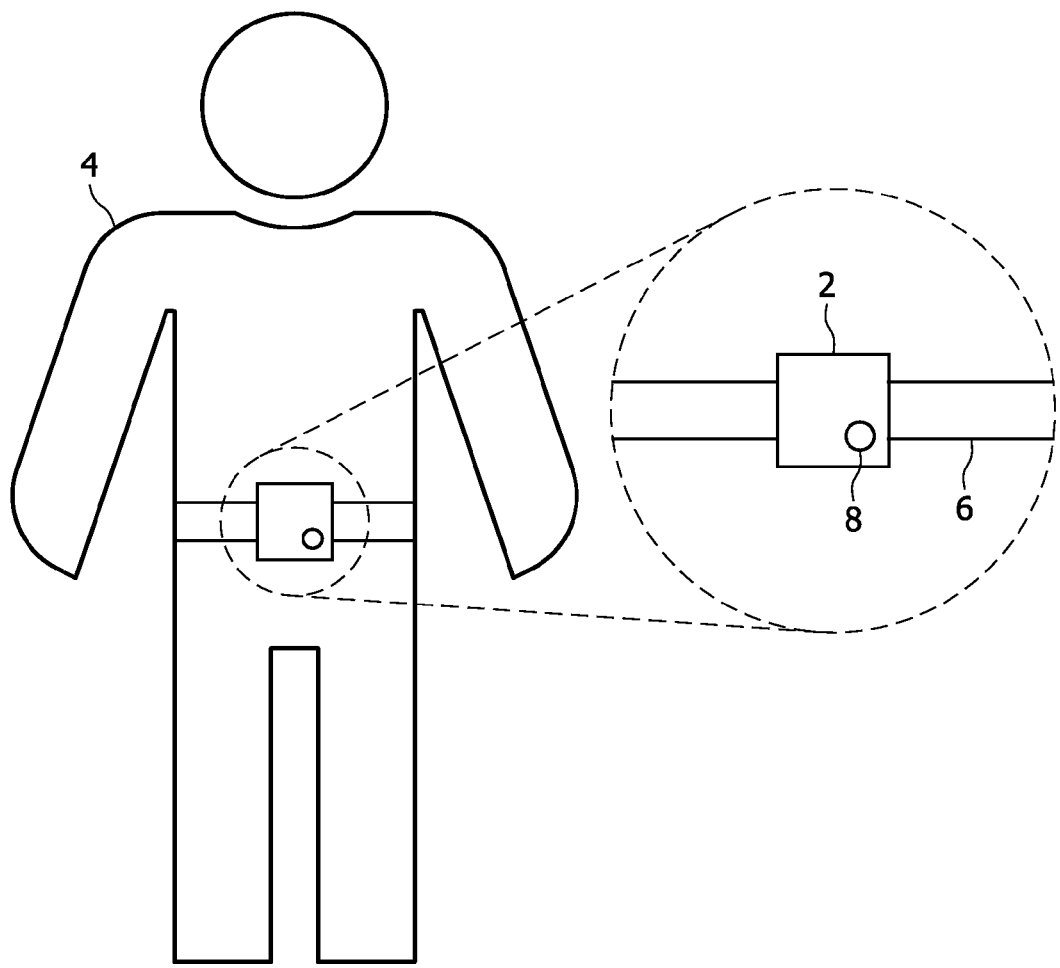
FIG. 1 shows a fall detection system attached to a user.

FIG. 1 shows a fall detection system 2 attached to a user 4 via a band or other attachment means 6. The fall detection system 2 is preferably attached at the upper part of the user's body 4, such as around the waist, at the wrist, or as a pendant around the neck.

In this embodiment, the fall detection system 2 includes an alarm reset button 8 that the user 4 can operate to prevent or stop an alarm signal being sent to a call-centre or other assistance unit. Thus, if the fall detection system 2 detects a fall by the user 4, an alarm signal will be sent to a call-centre or other assistance unit, unless the user 4 indicates that a fall has not taken place by pressing the alarm reset button 8. This is considered to be a false positive (FP).

In this case, the fall detection algorithm executing in the system 2 is considered to have incorrectly identified a fall from the signals received from the sensors. It may be that the criteria or parameters used to identify falls from the received signals are not set at an appropriate level for the particular user 4 of the system 2, so it is desirable to train or adapt the fall detection algorithm to the particular characteristics (for example gait and balance) of the user 4. In addition, it is desirable for the fall detection algorithm to learn the types of situations or falls for which the user does or does not require assistance. Near falls for which the user 4 does not require call-centre intervention can be used to train the algorithm to classify them as non-falls.

In addition, if the user 4 does fall but stands up again, user 4 may want to decide him/herself whether assistance is needed and the fall detection system 2 should not alarm autonomously. For example, system 2 may observe the duration of the time period of relative constant acceleration when user 4 is lying down after a fall and before they stand up. If this period exceeds a threshold, the final decision on a fall is made and an alarm is sent to the call centre.

Suppressing this alarm, possibly even before the period reaches the threshold indicates that this time-out period should be extended for user 4. Also, the other way around, calling for help, i.e. pressing the alarm button (if present)

before the period reaches the threshold, indicates the threshold of the time-out period needs to be shortened.

Figure 2:
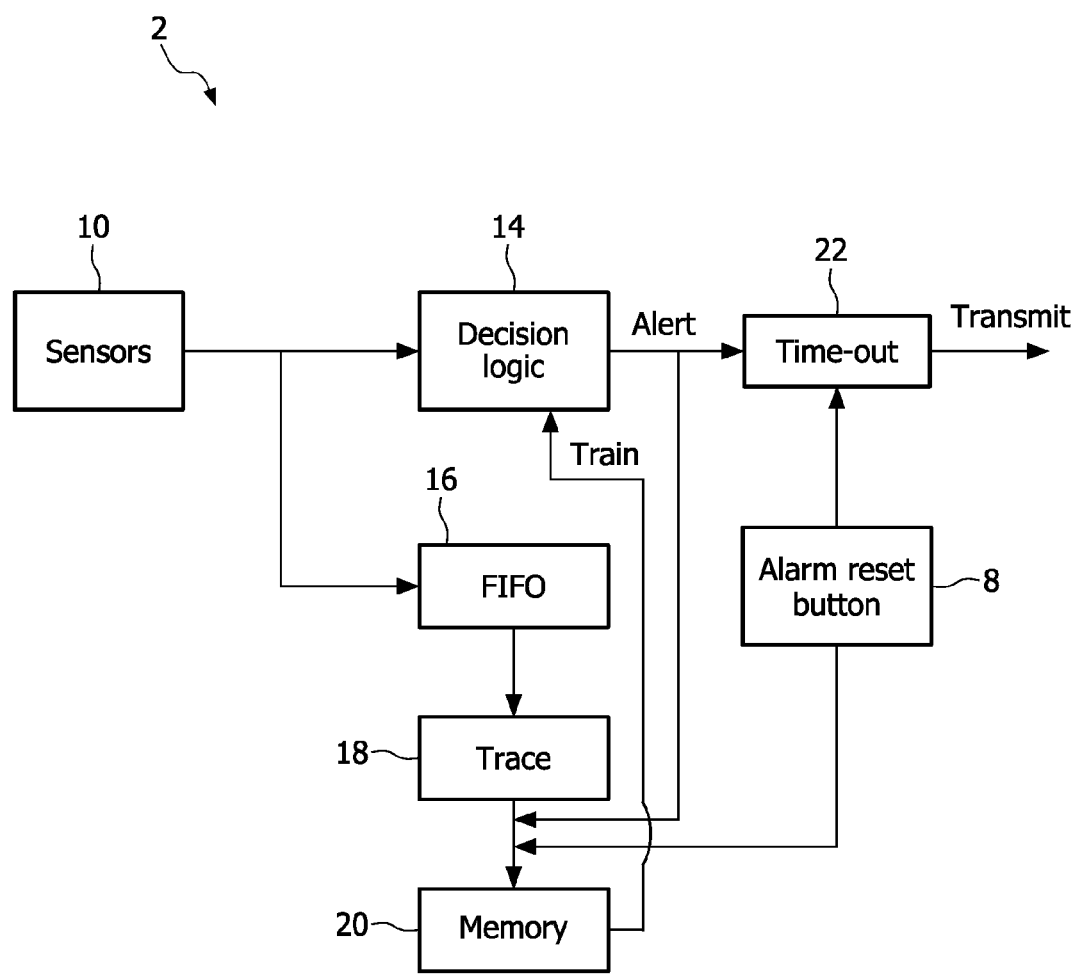
FIG. 2 is a block diagram of the fall detection system.

FIG. 2 is a block diagram of a fall detection system 2 in accordance with the invention.

The system 2 comprises one or more sensors 10 that detect characteristics of movement of the user 4 and that generate corresponding signals. The one or more sensors 10 can comprise an accelerometer, magnetometer, gyroscope and/or other sensors.

The signals from the sensor(s) 10 form a feature set, possibly after some processing. Exemplary features include magnitude, spectral content, directional distribution, mean, variance, etc., but alternatively the signals themselves, i.e. the time series of sample values, can serve as feature set. The features are provided to decision logic 14 that executes the fall detection algorithm. In particular, the decision logic 14 determines whether a fall has taken place by comparing the feature set to a set of parameters that are used to classify whether a fall has taken place or not. These parameters can include, or be based on, feature sets from known falls, or risky situations.

At least a subset of the signals, or the extracted features, from the sensor(s) 10 are also provided to a FIFO buffer 16 that temporarily stores them for a predetermined time period. The duration of this time period can be different for different parts of the stored signals and features. For example, subsampling may be applied after passing a first time period. The stored signals and features are provided from the FIFO buffer 16 to a trace generating unit 18 that generates a trace for the signals that can be selectively stored in a memory 20. A trace is generated in case a fall is detected by the decision logic 14 or in case the alarm reset button 8 has been pressed. The state of the decision logic 14 (fall/no-fall) as well as of the button 8 (pressed/not-pressed) is labeled with the trace.

If the decision logic 14 determines that a fall has taken place, an alarm signal is generated and sent to a time-out unit 22. The time-out unit 22 is connected to the alarm reset button 8, and, if the time-out unit 8 receives an alarm reset signal from the button 8 within a predetermined time-out period (which may be zero), the alarm signal is stopped. Otherwise, if no alarm reset signal is received within the time-out period, the alarm signal is transmitted to a call-centre or other assistance point. Alternatively, the alarm may be issued immediately to the call-centre, and a reset signal sends a revocation to the call-centre.

It should be noted that, in alternative embodiments, the fall detection system 2 can comprise a sensor unit for attachment to a user and a separate base station that receives the signals from the sensor unit and hosts the processing required to detect falls and generate alarm signals. In further alternative embodiments, the processing can be located at the call centre or at an intermediate location between the system 2 and call centre.

The complete trace, i.e. the signal and/or features from the FIFO 16 and states of decision logic 14 and button 8, are provided to the memory 20.

In some embodiments, as suggested above, the alarm reset button 8 can also be used by the user 4 to indicate that a fall has taken place, in the event that a fall is not detected by the system 2. In this case, if the decision logic 14 does not detect a fall from the feature set, but the alarm reset button 8 is pressed, an alarm signal can be transmitted. In addition, the signal from the decision logic 14 indicating that no fall has been detected is provided to the memory 20, along with the signal from the alarm reset button 8, where they are stored with the relevant signal trace.

If no alert is generated by the decision logic 14 and the alarm-reset button 8 is not pressed, the relevant feature sets that led to this decision can be discarded from the FIFO buffer 16. In these cases, the decision logic 14 has correctly identified from the features sets that no fall has taken place, or that no fall is likely to take place.

In alternative embodiments, an alarm button can be provided in addition to the alarm reset button 8 for allowing the user 4 to explicitly indicate that a fall has taken place (whether or not the algorithm has detected a fall), or that assistance is required. In this embodiment, if the decision logic 14 does not detect a fall from the feature set, but the alarm button is pressed, an alarm signal can be transmitted. The signal from the alarm button is provided to the memory 20 where it is stored with the trace of the signals from the sensor(s) 10.

Thus, the fall detection system 2, which can comprise a single accelerometer, is extended with a storage system 16, 18, 20 that is dedicated to store a feature set of the signals from the accelerometer. Raw sensor signals from the accelerometer can also be stored in cases where this is more efficient, for example when the decision logic 14 is based on direct signal characteristics, such as a threshold of the magnitude or frequency of the signal. In addition to the signal and/or its feature set, other data can be stored, such as time stamp data. It should be appreciated that, although not shown in the illustrated embodiment, the storage system can be physically remote from the accelerometer (i.e. remote from the device attached to the user 4). Timing data can be relative, indicating the progression within one trace of subsequent feature sets.

During operation, feature sets are stored in the memory 20 and are analyzed by the decision logic 14 for characterizing a fall, in case of fall detection, or an increased risk for falling, in case of fall prevention. Clearly, the algorithm can be used in both fall detection and fall prevention. The algorithm can use the stored data directly, i.e. compare current signal/features with those in memory 20. It can also use the stored data indirectly, in which case the algorithm maintains internal settings and thresholds which are regularly adapted during an update process based on the (new) data stored in memory 20. An update can be triggered upon each change in memory 20 (trace added or trace removed), or after a certain number of changes, possibly combined with a time out. An (additional) update can also be triggered if the rate at which memory 20 is updated changes.

As described above, if the alarm-reset button 8 is pressed, the trace of feature sets in the buffer is copied into the memory 20, where it will be kept for a possibly indefinite length of time. Next to the trace data, the decision value is stored. Thus, in the case that the decision logic 14 has raised an alert, but the alarm reset button 8 is pressed, the trace data is labeled to represent a FP. In the case of no alert, but there is an indication from the user 4 that there was a fall, the trace data is labeled to represent a FN. Trace data raising an alert and for which no button press has been received can be stored as a TP (true positive). Optionally, signals and feature sets that do not raise a fall detection by the decision logic 14 and which are neither labeled with an (alarm) button press can be stored as well, labeled as TN (true negative). This may help the training of the adaptive algorithm.

In order to adapt to possible changes in the user's characteristics, e.g. related to ageing, traces in memory 20 may expire. Expiration can be triggered by similar mechanisms as the updating of the decision algorithm 14. Expiration itself can trigger such an update.

At first use of the fall detection system 2, the memory 20 and the algorithm 14 can be loaded with values that represent the characteristics of the population in general. These values, or part of them, can be labeled to expire in any case, or to expire in a shorter time period, e.g. as soon as a sufficient amount of user specific data has been collected.

In the alternative embodiment where separate buttons may be present for performing an alarm reset and for activating the alarm, traces representing TP can be selected based on the explicit alert presses (together with a generated alert).

In accordance with the invention, the stored information is used to adapt or train the algorithm used in the decision logic 14 to reduce the rates of false positives and false negatives. Thus, the decision logic 14 is trained using the trace data and the associated button press status (i.e. was a reset button 8 pressed?) or the trace data and associated status, FP, FN or TP.

The algorithm used in decision logic 14 can be updated each time that a button 8 is pressed, or can be updated every five button presses, say. Alternatively, the algorithm can be updated after a given period of time has passed, or any combination of the above.

In this way, the algorithm used in the decision logic 14 will become personalized to moving patterns of the user 4. In addition, in the case of fall prevention, the algorithm will learn what situations the user 4 considers risky. In preferred embodiments, by obtaining data from multiple sensors 10 and sensor types, the measurable space of these risky situations will be expanded.

In particular, in the case of fall prevention, physiological data is of interest, such as characteristics indicating dizziness, and including quantities like blood pressure, oxygen level (SPO2), heart rate (ECG), muscle activity and fatigue (EMG and MMG), temperature, lung sounds, etc.

If the fall detection system 2 correctly classifies a non-risk situation (i.e. correctly in terms of the trained algorithm with its reference data and user feedback), but is succeeded closely by a fall, the system 2 can revisit its risk and non-risk categories and classify the traces therein with reference to earlier data (from other people, or from initial or factory settings). In this way, it is possible to identify those traces in the training set that are labelled as non-risky but are classified as risky in the earlier reference data. These traces can be refracted from the personalized training set, after which the decision algorithm can be trained again.

A refinement for the updating algorithm is to check the update rate, i.e. the time interval between subsequent button presses. If the intervals are small, this can indicate that the algorithm has a suboptimal adaptation state (i.e. the algorithm is frequently generating false positives or false negatives), whereas long intervals, or saturation in getting longer, indicates that optimality is reached. In particular, if the update rate increases (i.e. the intervals get shorter), this may indicate the algorithm is becoming "over fitted", or too specific/narrow. To prevent this, samples (i.e. traces) can be removed from the training set. However, this process should also take into account that there may be changes in the user's moving patterns (gait & balance). For example, the user's ability to maintain balance can decline over time. This latter information can, for example, be entered on the basis of the regular examination by the user's general practitioner.

The computation for determining the time interval between updates can also be adapted to the user's activities. For example, if the user takes off or switches off the fall detection system 2, this time should not be counted towards an update interval. Similarly, if the user tends to sit steadily or stay in bed for long time periods, the update time interval computation can take this into account. In some embodiments, the time intervals can be computed relative to the average duration between instants where, say, the measured acceleration exceeds a or some reference thresholds.

In some embodiments, another measure that can be used to estimate the optimality of the algorithm is a stable ratio between FP and FN rates, or between TP and FP rates. This indicates that further improvement of the algorithm (in terms of reducing FP and FN) is not possible without the addition of additional or other types of sensor signals. In some embodiments, the user 4 can be informed of the ratio. It is also possible for the user 4 to be provided with the ability to set the ratio is considered optimal. For example, "no FN" can be a setting, and the ratio can be used to train and tune the algorithm accordingly.

In further embodiments of the invention, instead of solely labeling the traces on the basis of the alarm-reset button 8 (or an alarm button) being pressed, other interventions can trigger the described storing and training process as well. For example, a care provider may observe a near-fall or a risky situation and trigger the system 2 to use the data for training. This trigger may comprise the care provider pressing the button 8 on the system 2, or the care provider remotely sending a signal to the system 2.

The stored patterns or traces can also be set apart for inspection by the care provider or general practitioner. In particular, if they have been labeled as false positive by the user 4, the care provider can use the data as a report to form an expert opinion on the well-being (and the trend therein) of the user 4. Possibly, the care provider can decide to override the user's label to consider the incident a false positive.

In addition to the user 4 initiating the training of the algorithm when an alarm reset/alarm button is pressed, a care provider or care centre can also initiate the training update. For example, if an alert reaches the call centre and the user does not issue an alert-reset, while the care centre finds out if it was a false alarm, the care centre can send a training command to the system 2.

Figure 3:
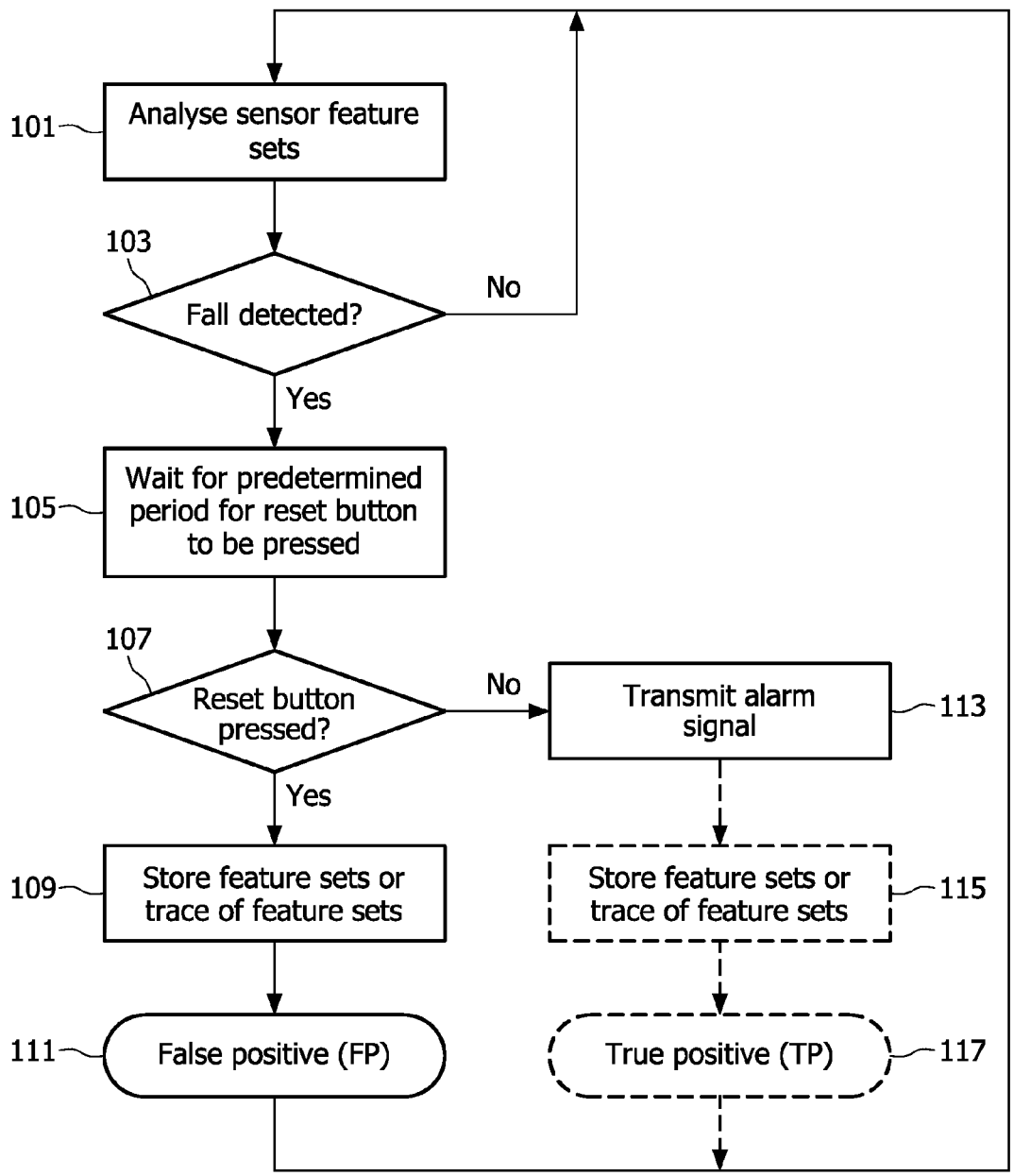
FIG. 3 is a flow chart illustrating a first method in accordance with the invention.

Referring now to FIG. 3, the method of operating a fall detection system 2 that has an alarm reset button 8 is presented. In step 101, a feature set is received from the sensor(s) 10 and is analyzed using the fall detection algorithm in the decision logic 14. If a fall is not detected (step 103), the process returns to step 101 where a subsequent feature set is analyzed.

If a fall is detected (step 103), the process moves to step 105 where the fall detection system 2 waits for a predetermined period for the alarm reset button 8 to be pressed.

If the reset button 8 is pressed (step 107), the feature set or a trace of the feature set is stored in a memory 20 (step 109). This feature set or trace is stored along with the alarm reset indication, which means that it is stored as a false positive (step 111). The process then returns to step 101.

If the reset button 8 is not pressed (step 107), an alarm signal is transmitted (step 113). In alternative embodiments, step 113 can also be triggered directly by a 'yes' at step 103, in which case 'yes' by step 107 can raise a revocation.

Optionally (as indicated by the dashed arrows and boxes), the feature set or a trace of the feature set is stored in a memory 20 (step 115) along with an indication that the alarm reset button 8 was not pressed, which means that it is stored as a true positive (step 117). In either case, the process then returns to step 101.

Figure 4:
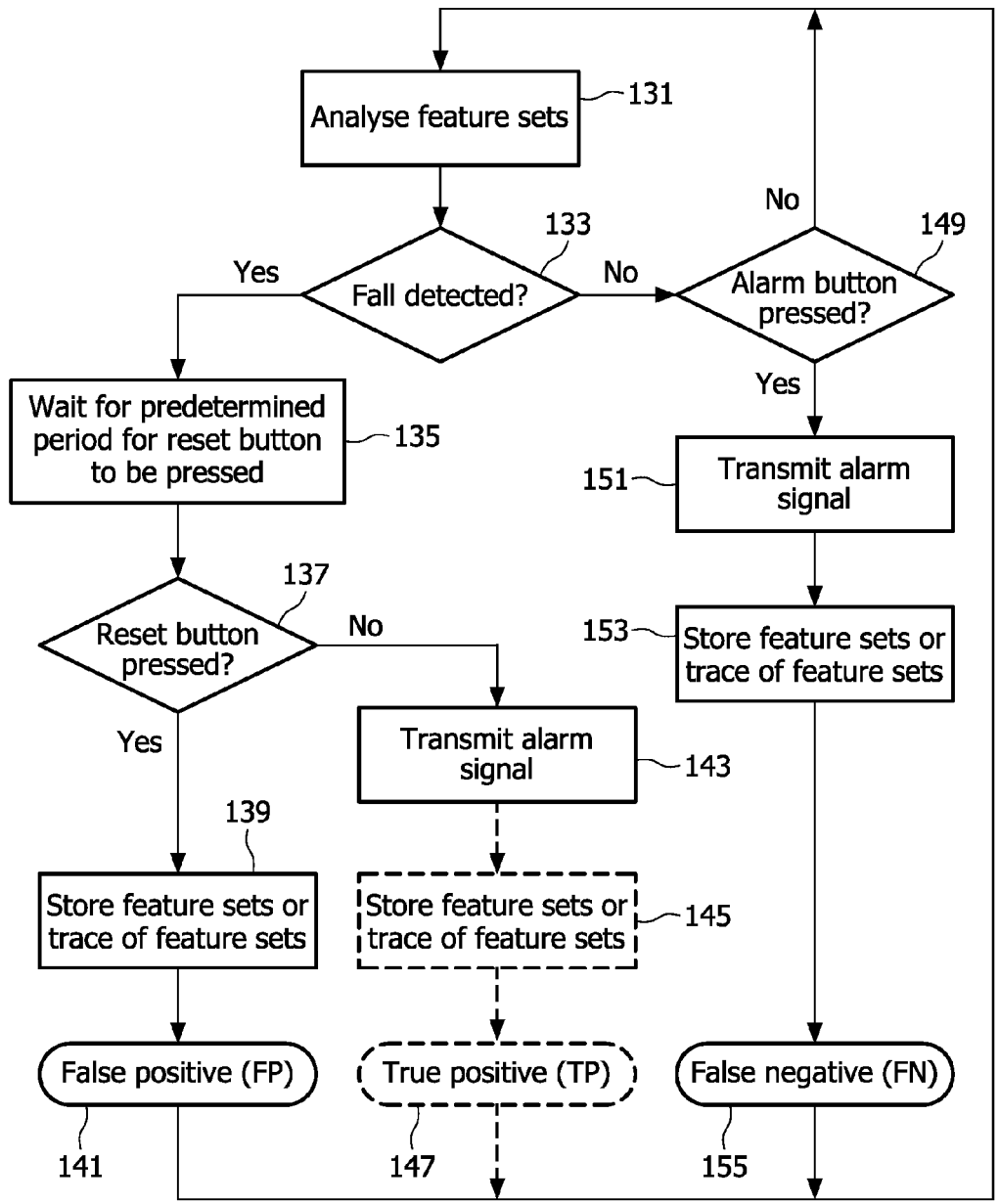
FIG. 4 is a flow chart illustrating a second method in accordance with the invention.

A method of operating a fall detection system 2 that has both an alarm reset button 8 and an alarm button is shown in FIG. 4. In step 131, a feature set is received from the sensor(s) 10 and is analyzed using the fall detection algorithm in the decision logic 14.

If a fall is detected (step 133), the process moves to step 135 where the fall detection system 2 waits for a predetermined period for the alarm reset button 8 to be pressed.

If the reset button 8 is pressed (step 137), the feature set or a trace of the feature set is stored in a memory 20 (step 139). This feature set or trace is stored along with the alarm reset indication, which means that it is stored as a false positive (step 141). The process returns to step 131 where a subsequent feature set is analyzed.

If the reset button 8 is not pressed (step 137), an alarm signal is transmitted (step 143). Step 143 can also be triggered directly by a 'yes' at step 133, in which case 'yes' by step 137 can raise a revocation.

Optionally (as indicated by the dashed arrows and boxes), the feature set or a trace of the feature set is stored in a memory 20 (step 145) along with an indication that the alarm reset button 8 was not pressed, which means that it is stored as a true positive (step 147). Alternatively, or in addition, if the alarm button was pressed, the feature set can be stored in the memory 20 along with an indication that this alarm button was pressed. The process can then return to step 101.

If a fall is not detected at step 133, it is determined whether the alarm button has been pressed (step 149). If the alarm button is not pressed, then no fall has occurred, and the process returns to step 131.

If the alarm button is pressed, an alarm signal is transmitted (step 151), and the feature set or a trace of the feature set is stored in the memory 20, along with an indication that the alarm button was pressed (step 153). Thus, this is stored as a false negative (step 155).

The process then returns to step 131.

Figure 5:
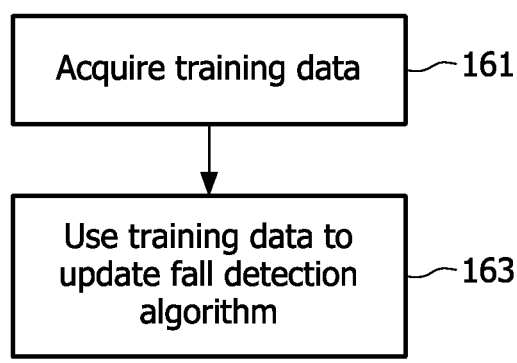
FIG. 5 is a flow chart illustrating a method of training a fall detection algorithm in accordance with the invention.

FIG. 5 is a flow chart illustrating the steps in the method of training or adapting the fall detection algorithm in accordance with the invention. In step 161, suitable training data is acquired. This training data, which comprises feature sets or traces of feature sets, along with indications of whether the feature sets were false positives, false negatives and/or true positives, can be acquired as described above with reference to FIGS. 3 and 4.

Then, in step 163, this training data is used to update the fall detection algorithm. In particular, if the fall detection algorithm includes a category or categories of feature sets or traces that indicate falls or non-falls, the newly acquired training data can be used to further populate those categories and/or be used to remove existing feature sets or traces, if it has now been found that those existing feature sets or traces are not appropriate for that category.

Thus, there is provided a fall detection system that can be adapted to a particular user's fall or activity characteristics in order to improve the reliability of the fall detection algorithm. In particular, the training data for the algorithm is generated from sensor measurements and on whether an alarm reset button is pressed by a user or care provider. In this way, the algorithm used for detecting falls or near falls can be trained as the detection system 2 is in use, so realistic data can be obtained and used in the training, rather than being artificially created by a user mimicking a fall or non-fall in a specific training phase, as in conventional systems. In addition, by training the algorithm for a particular user, the algorithm will be adapted to the particular physical characteristics of that user, such as gait and posture, that user's movement patterns and that user's opinion on the severity of falls that require assistance from a call centre.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall detection and/or prevention system, comprising:
   one or more sensors for detecting characteristics of movement of a user of the fall detection and/or prevention system and for generating corresponding signals;
   one or more computers for analyzing the signals from the one or more sensors using a fall detection algorithm to determine if a fall has taken place or is likely to take place, the fall detection algorithm including one or more feature sets indicating falls or non-falls and representing signals from the one or more sensors, the one or more computers being configured to:
   update said fall detection algorithm based on the result of the analysis of the signals using the fall detection algorithm to determine if a fall has taken place or is likely to take place and an indication as to whether a fall has actually taken place from the user or a third party, and
   monitor the frequency with which the fall detection algorithm is updated, and if the frequency exceeds a threshold, remove one or more feature sets from the fall detection algorithm.

2. The fall detection and/or prevention system as claimed in claim 1, wherein the one or more computers are further configured to generate an alarm signal in the event that a fall has taken place or is likely to take place.

3. The fall detection and/or prevention system as claimed in claim 1, further comprising:
   a memory configured to store the one or more feature sets, an indication from the fall detection algorithm of whether the fall detection algorithm has determined that a fall has taken place or is likely to take place, and the indication whether a fall has actually taken place.

4. The fall detection and/or prevention system as claimed in claim 1, wherein the indication whether a fall has actually taken place comprises a reset signal.

5. The fall detection and/or prevention system as claimed in claim 4, wherein one or more computers are further configured to:
   determine whether the fall detection algorithm has provided a false positive in the event that the fall detection algorithm detects that a fall has taken place and the reset signal is present, and update the fall detection algorithm accordingly.

6. The fall detection and/or prevention system as claimed in claim 4, wherein the one or more computers are further configured to:
   determine whether the fall detection algorithm has provided a true positive in the event that the fall detection algorithm detects that a fall has taken place and the reset signal is not present, and
   update the fall detection algorithm accordingly.

7. The fall detection and/or prevention system as claimed in claim 4, further comprising:
an input which receives the reset signal from a third party.

8. The fall detection and/or prevention system as claimed in claim 4, further comprising a first user operable component for allowing a user to selectively generate the reset signal.

9. The fall detection and/or prevention system as claimed in claim 8, further comprising a second user-operable component for generating an alarm signal.

10. The fall detection and/or prevention system as claimed in claim 9, wherein the one or more processors are further configured to:
determine whether the fall detection algorithm has provided a false negative in the event that the fall detection algorithm does not detect that a fall has taken place and the alarm signal is present, and
update the fall detection algorithm accordingly.

11. The fall detection and/or prevention system as claimed in claim 9, wherein the one or more processors are further configured to:
determine whether the fall detection algorithm has provided a true positive in the event that the fall detection algorithm detects that a fall has taken place and the alarm signal is present, and update the fall detection algorithm accordingly.

12. The fall detection and/or prevention system as claimed in claim 1, wherein the fall detection algorithm comprises one or more feature sets representing signals from the one or more sensors.

13. A fall detection and/or prevention system comprising:
one or more sensors configured to detect characteristics of movement of a user and generate signals corresponding to the detected characteristics of movement;
a computer which analyzes signals from the one or more sensors using a fall detection algorithm which includes one or more features sets representing signals from the one or more sensors to determine if a fall has taken place or is likely to take place, the computer being configured to:
update said fall detection algorithm based on the result of the analysis of the signals and an indication whether a fall has actually taken place from the user or a third party;
monitor the frequency with which the fall detection algorithm is updated, and
if the frequency exceeds a threshold, remove one or more feature sets from the fall detection algorithm.

14. The fall detection and/or prevention system as claimed in claim 12, wherein the one or more computers are configured to determine whether a fall has taken place or is likely to take place by comparing the one or more feature sets with the corresponding signals generated by the one or more sensors.

15. The fall detection and/or prevention system as claimed in claim 1, wherein the one or more computers are configured to update the fall detection algorithm to selectively optimize false positives, in response to:
the algorithm incorrectly detecting a fall or false negatives, or
incorrectly detecting that no fall has taken place to obtain a stable ratio between false positives and false negatives.

16. A non-transitory computer-readable medium carrying computer executable code that, when executed on a computer or processor, controls the computer or processor to perform the steps of:
receiving signals indicating characteristics of movement of a user of a fall detection and/or prevention system;
analyzing the signals using a fall detection algorithm which includes a plurality of movement characteristics feature sets to determine if a fall has taken place or is likely to take place;
updating said fall detection algorithm based on the result of the analysis of the signals and an indication whether a fall has actually taken place; and
in response to a frequency with which the fall detection algorithm is updated exceeding a threshold, removing one or more of the feature sets.

17. A method of training a fall detection and/or prevention algorithm for use in a fall detection and/or prevention system, the method comprising:
with movement sensors, obtaining measurements of characteristics of movement of a user;
with one or more computers, analyzing the measurements using a fall detection algorithm which compares characteristics of movement feature sets to determine if a fall has taken place or is likely to take place and updating said fall detection algorithm based on an indication whether a fall has actually taken place and removing at least one of the feature sets in response to a frequency with which the fall detection algorithm is updated exceeding a threshold.

18. The method as claimed in claim 17, wherein the one or more computers update the fall detection algorithm in response to:
the fall detection algorithm determining that a fall has or is likely to take place and an input from the user or a third party indicating no fall has taken place; or
the fall detecting algorithm not determining that a fall has or is likely to take place and an input from the user or a third party indicating a fall has taken place.

* * * * *